United States Patent
Orszulak

(10) Patent No.: US 9,044,238 B2
(45) Date of Patent: Jun. 2, 2015

(54) ELECTROSURGICAL MONOPOLAR APPARATUS WITH ARC ENERGY VASCULAR COAGULATION CONTROL

(75) Inventor: James H. Orszulak, Nederland, CO (US)

(73) Assignee: Covidien LP, Mansfield, MA (US)

(*) Notice: Subject to any disclaimer, the term of this patent is extended or adjusted under 35 U.S.C. 154(b) by 476 days.

(21) Appl. No.: 13/443,710

(22) Filed: Apr. 10, 2012

(65) Prior Publication Data

US 2013/0267947 A1  Oct. 10, 2013

(51) Int. Cl.
*A61B 18/00* (2006.01)
*A61B 18/12* (2006.01)
*A61B 17/32* (2006.01)
*A61B 18/14* (2006.01)
*A61B 18/18* (2006.01)

(52) U.S. Cl.
CPC ... *A61B 18/1233* (2013.01); *A61B 2018/00345* (2013.01); *A61B 2018/00589* (2013.01); *A61B 2018/00642* (2013.01); *A61B 2018/00666* (2013.01); *A61B 2018/00779* (2013.01); *A61B 2018/00827* (2013.01); *A61B 2018/00892* (2013.01); *A61B 2018/1213* (2013.01); *A61B 17/320068* (2013.01); *A61B 18/1445* (2013.01); *A61B 18/1815* (2013.01); *A61B 2018/00607* (2013.01); *A61B 2018/0063* (2013.01); *A61B 2018/00702* (2013.01); *A61B 2018/00875* (2013.01)

(58) Field of Classification Search
USPC ............... 606/32, 34, 37–40, 45, 48–52
See application file for complete search history.

(56) References Cited

U.S. PATENT DOCUMENTS

| 730,557 | A | 6/1903 | McElroy |
| 4,114,623 | A | 9/1978 | Meinke et al. |
| 4,188,927 | A | 2/1980 | Harris |
| 4,196,734 | A | 4/1980 | Harris |
| 4,271,837 | A | 6/1981 | Schuler |
| 4,429,694 | A | 2/1984 | McGreevy |
| 4,590,934 | A | 5/1986 | Malis et al. |
| 4,727,874 | A | 3/1988 | Bowers et al. |

(Continued)

FOREIGN PATENT DOCUMENTS

| EP | 0 870 473 B1 | 10/1998 |
| EP | 1 500 378 A1 | 1/2005 |

(Continued)

OTHER PUBLICATIONS

International Search Report from corresponding Application No. EP 13163227.5 dated Jun. 13, 2013.

(Continued)

*Primary Examiner* — Paula J Stice

(57) ABSTRACT

A system for delivering electrosurgical energy is provided. The system includes an electrosurgical instrument comprising at least one electrode and an electrosurgical generator coupled to the electrosurgical instrument. The electrosurgical generator includes an output stage configured to generate electrosurgical energy; and a controller coupled to the output stage, the controller configured to control the output stage to output electrosurgical energy at a predetermined power level to generate an arc between the at least one electrode and tissue and to output electrosurgical energy at a predetermined current level once the arc is generated to sustain the arc.

16 Claims, 4 Drawing Sheets

(56) References Cited

U.S. PATENT DOCUMENTS

| | | |
|---|---|---|
| 4,860,745 A | 8/1989 | Farin et al. |
| 5,152,762 A | 10/1992 | McElhenney |
| 5,244,462 A | 9/1993 | Delahuerga et al. |
| RE34,432 E | 11/1993 | Bertrand |
| 5,370,645 A | 12/1994 | Klicek et al. |
| 5,372,596 A | 12/1994 | Klicek et al. |
| 5,451,224 A | 9/1995 | Goble et al. |
| 5,556,396 A | 9/1996 | Cohen et al. |
| 5,749,869 A | 5/1998 | Lindenmeier et al. |
| 5,827,271 A | 10/1998 | Buysse et al. |
| 5,846,236 A | 12/1998 | Lindenmeier et al. |
| 5,891,142 A | 4/1999 | Eggers et al. |
| 5,954,717 A | 9/1999 | Behl et al. |
| 5,971,980 A | 10/1999 | Sherman |
| 6,022,347 A | 2/2000 | Lindenmeier et al. |
| 6,033,399 A | 3/2000 | Gines |
| 6,056,746 A | 5/2000 | Goble et al. |
| 6,080,149 A | 6/2000 | Huang et al. |
| 6,093,186 A | 7/2000 | Goble |
| 6,123,702 A | 9/2000 | Swanson et al. |
| 6,142,992 A | 11/2000 | Cheng et al. |
| 6,183,468 B1 | 2/2001 | Swanson et al. |
| 6,228,080 B1 | 5/2001 | Gines |
| 6,245,065 B1 | 6/2001 | Panescu et al. |
| 6,261,286 B1 | 7/2001 | Goble et al. |
| 6,287,304 B1 | 9/2001 | Eggers et al. |
| 6,293,942 B1 | 9/2001 | Goble et al. |
| 6,306,134 B1 | 10/2001 | Goble et al. |
| 6,364,877 B1 | 4/2002 | Goble et al. |
| 6,398,779 B1 | 6/2002 | Buysse et al. |
| 6,416,509 B1 | 7/2002 | Goble et al. |
| 6,494,880 B1 | 12/2002 | Swanson et al. |
| 6,582,427 B1 | 6/2003 | Goble et al. |
| 6,685,700 B2 | 2/2004 | Behl et al. |
| 6,696,844 B2 | 2/2004 | Wong et al. |
| 6,758,846 B2 | 7/2004 | Goble et al. |
| 6,796,981 B2 | 9/2004 | Wham et al. |
| 6,837,888 B2 | 1/2005 | Ciarrocca et al. |
| 6,843,789 B2 | 1/2005 | Goble |
| 6,893,435 B2 | 5/2005 | Goble |
| 6,939,347 B2 | 9/2005 | Thompson |
| 6,942,660 B2 | 9/2005 | Pantera et al. |
| 6,953,461 B2 | 10/2005 | McClurken et al. |
| 6,974,453 B2 | 12/2005 | Woloszko et al. |
| 7,001,379 B2 | 2/2006 | Behl et al. |
| 7,156,846 B2 | 1/2007 | Dycus et al. |
| 7,195,627 B2 | 3/2007 | Amoah et al. |
| 7,211,081 B2 | 5/2007 | Goble |
| 7,220,260 B2 | 5/2007 | Fleming et al. |
| 7,364,577 B2 | 4/2008 | Wham et al. |
| RE40,388 E | 6/2008 | Gines |
| 7,470,272 B2 | 12/2008 | Mulier et al. |
| 7,513,896 B2 | 4/2009 | Orszulak |
| 7,582,084 B2 | 9/2009 | Swanson et al. |
| 7,651,492 B2 | 1/2010 | Wham |
| 7,666,182 B2 | 2/2010 | Klett et al. |
| 7,678,105 B2 | 3/2010 | McGreevy et al. |
| 7,799,020 B2 | 9/2010 | Shores et al. |
| 7,972,328 B2 | 7/2011 | Wham et al. |
| 7,976,544 B2 | 7/2011 | McClurken et al. |
| 8,147,485 B2 | 4/2012 | Wham et al. |
| 2002/0029036 A1 | 3/2002 | Goble et al. |
| 2003/0153908 A1 | 8/2003 | Goble et al. |
| 2003/0199863 A1 | 10/2003 | Swanson et al. |
| 2003/0229344 A1 | 12/2003 | Dycus et al. |
| 2004/0030330 A1 | 2/2004 | Brassell et al. |
| 2004/0230189 A1 | 11/2004 | Keppel |
| 2006/0111711 A1 | 5/2006 | Goble |
| 2007/0173804 A1 | 7/2007 | Wham et al. |
| 2007/0173810 A1 | 7/2007 | Orszulak |
| 2007/0173811 A1 | 7/2007 | Couture et al. |
| 2007/0250052 A1 | 10/2007 | Wham |
| 2007/0282320 A1 | 12/2007 | Buysse et al. |
| 2008/0015563 A1* | 1/2008 | Hoey et al. ............... 606/34 |
| 2008/0071260 A1 | 3/2008 | Shores |
| 2008/0082095 A1 | 4/2008 | Shores et al. |
| 2008/0281315 A1 | 11/2008 | Gines |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0248007 A1 | 10/2009 | Falkenstein et al. |
| 2009/0254077 A1 | 10/2009 | Craig |
| 2009/0259224 A1 | 10/2009 | Wham et al. |
| 2009/0275938 A1 | 11/2009 | Roggan et al. |
| 2010/0094275 A1 | 4/2010 | Wham |
| 2011/0028963 A1 | 2/2011 | Gilbert |

FOREIGN PATENT DOCUMENTS

| | | |
|---|---|---|
| EP | 1 609 430 B1 | 12/2005 |
| EP | 1 810 634 A1 | 7/2007 |
| EP | 1 849 425 B1 | 10/2007 |
| EP | 1 862 137 B1 | 12/2007 |
| EP | 2407116 A1 | 1/2012 |
| GB | 2 164 473 | 3/1986 |
| WO | WO 96/39086 | 12/1996 |
| WO | WO 97/10763 | 3/1997 |
| WO | WO 98/27880 | 7/1998 |
| WO | 2004030552 A1 | 4/2004 |
| WO | WO 2004/043240 | 5/2004 |
| WO | WO 2006/050888 | 5/2006 |

OTHER PUBLICATIONS

International Search Report from EP Appl. No. 11186103.5 dated Sep. 19, 2012.

* cited by examiner

ELECTROSURGICAL MONOPOLAR APPARATUS WITH ARC ENERGY VASCULAR COAGULATION CONTROL

BACKGROUND

1. Technical Field

The present disclosure relates to an electrosurgical system and method for operating an electrosurgical generator. More particularly, the present disclosure relates to a system, method and apparatus for controlling monopolar real-time arc energy vascular coagulation.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing surfaces). In addition, electrosurgical energy must be applied to the tissue under controlled conditions to ensure creation of an effective vessel seal.

Electrosurgical procedures outlined above may utilize various tissue and energy parameters in a feedback-based control system. There is continual need to improve delivery of energy to the tissue.

SUMMARY

According to one aspect of the present disclosure, a system for delivering electrosurgical energy is provided. The system includes an electrosurgical instrument comprising at least one electrode and an electrosurgical generator coupled to the electrosurgical instrument. The electrosurgical generator includes an output stage configured to generate electrosurgical energy; and a controller coupled to the output stage, the controller configured to control the output stage to output electrosurgical energy at a predetermined power level to generate an arc between the at least one electrode and tissue and to output electrosurgical energy at a predetermined current level once the arc is generated to sustain the arc.

According to another aspect of the disclosure, the electrosurgical generator further comprises a sensor configured to measure at least one of a tissue or an energy property.

According to an additional aspect of the disclosure, the controller is coupled to the sensor and is configured to switch between a power control mode and a current control mode in response to the at least one of the tissue or the energy property, wherein during the power control mode the output stage is delivering electrosurgical energy at the predetermined power level to generate an arc between the at least one electrode and tissue and during the current control mode the output stage is delivering electrosurgical energy at the predetermined current level once the arc is generated to sustain the arc.

In another aspect of the present disclosure, a system for delivering electrosurgical energy is provided. The system includes an electrosurgical instrument comprising at least one electrode and an electrosurgical generator coupled to the electrosurgical instrument. The electrosurgical generator includes an output stage configured to generate electrosurgical energy; a sensor configured to measure at least one of a tissue or an energy property; and a controller coupled to the output stage and the sensor, controller is configured to switch between a power control mode and a current control mode in response to the at least one of the tissue or the energy property, wherein during the power control mode the output stage is delivering electrosurgical energy at a predetermined power level to generate an arc between the at least one electrode and tissue and during the current control mode the output stage is delivering electrosurgical energy at a predetermined current level once the arc is generated to sustain the arc.

According to any of the above-described aspects, the sensor may be further configured to measure voltage applied to the tissue and the controller may be configured to determine whether the voltage is below a predetermined voltage threshold.

In further aspects, the controller is configured to maintain the current control mode in response to the voltage being below the predetermined voltage threshold.

According to a further aspect of the disclosure, the at least one of the tissue or the energy property is selected from the group consisting of impedance, root-mean-square voltage, average voltage, instantaneous voltage, current, power, root-mean-square current, average current, instantaneous current, root-mean-square power, average power, instantaneous power, and combinations thereof.

A method for delivering electrosurgical energy is also contemplated by the present disclosure. The method includes delivering electrosurgical energy at a predetermined power level to generate an arc between at least one electrode during a power control mode; and delivering electrosurgical energy at a predetermined current level once the arc is generated to sustain the arc during a current control mode.

In other aspects, the method further includes measuring at least one of a tissue or an energy property.

In additional aspects, the method further includes switching between the power control mode and the current control mode in response to the at least one of the tissue or the energy property.

The method also includes measuring a voltage applied to the tissue and determining whether the voltage is below a predetermined voltage threshold; and maintaining the current control mode in response to the voltage being below the predetermined voltage threshold.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cutting, blending, division, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
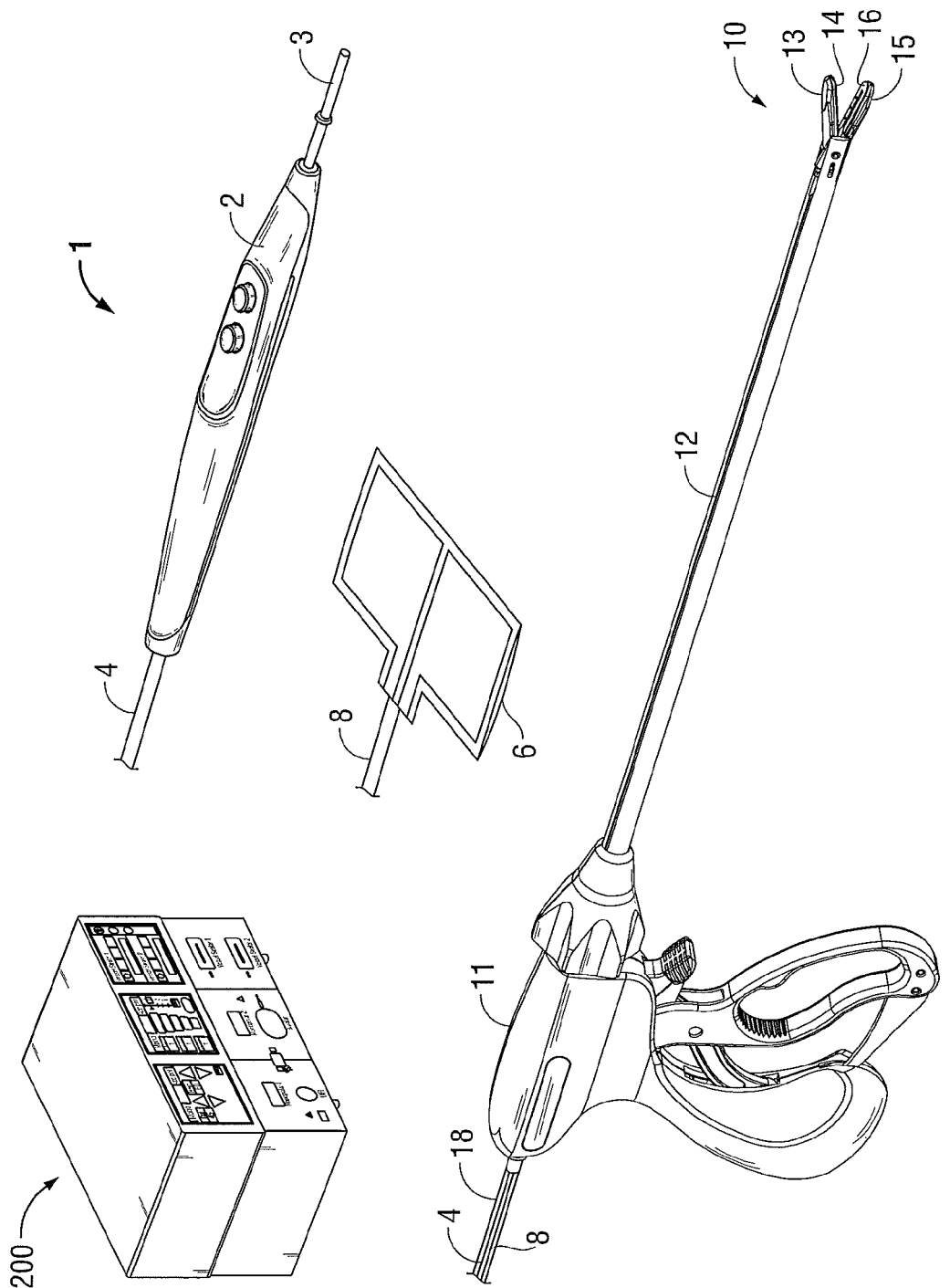
FIG. 1 is a schematic block diagram of an embodiment of an electrosurgical system according to the present disclosure.

FIG. 1 is a schematic illustration of a bipolar and monopolar electrosurgical system 1 according to the present disclosure. The system 1 may include one or more monopolar electrosurgical instruments 2 having one or more active electrodes 3 (e.g., electrosurgical cutting probe, ablation electrode(s), etc.) for treating tissue of a patient. Electrosurgical energy is supplied to the instrument 2 by a generator 200 via a supply line 4 that is connected to an active terminal 230 (FIG. 3) of the generator 200, allowing the instrument 2 to coagulate, ablate and/or otherwise treat tissue. The energy is returned to the generator 200 through a return electrode 6 via a return line 8 at a return terminal 232 (FIG. 3) of the generator 200. The system 1 may include a plurality of return electrodes 6 that are disposed on a patient to minimize the chances of tissue damage by maximizing the overall contact area with the patient. In addition, the generator 200 and the return electrode 6 may be configured for monitoring so-called "tissue-to-patient" contact to insure that sufficient contact exists therebetween to further minimize chances of tissue damage.

Figure 3:
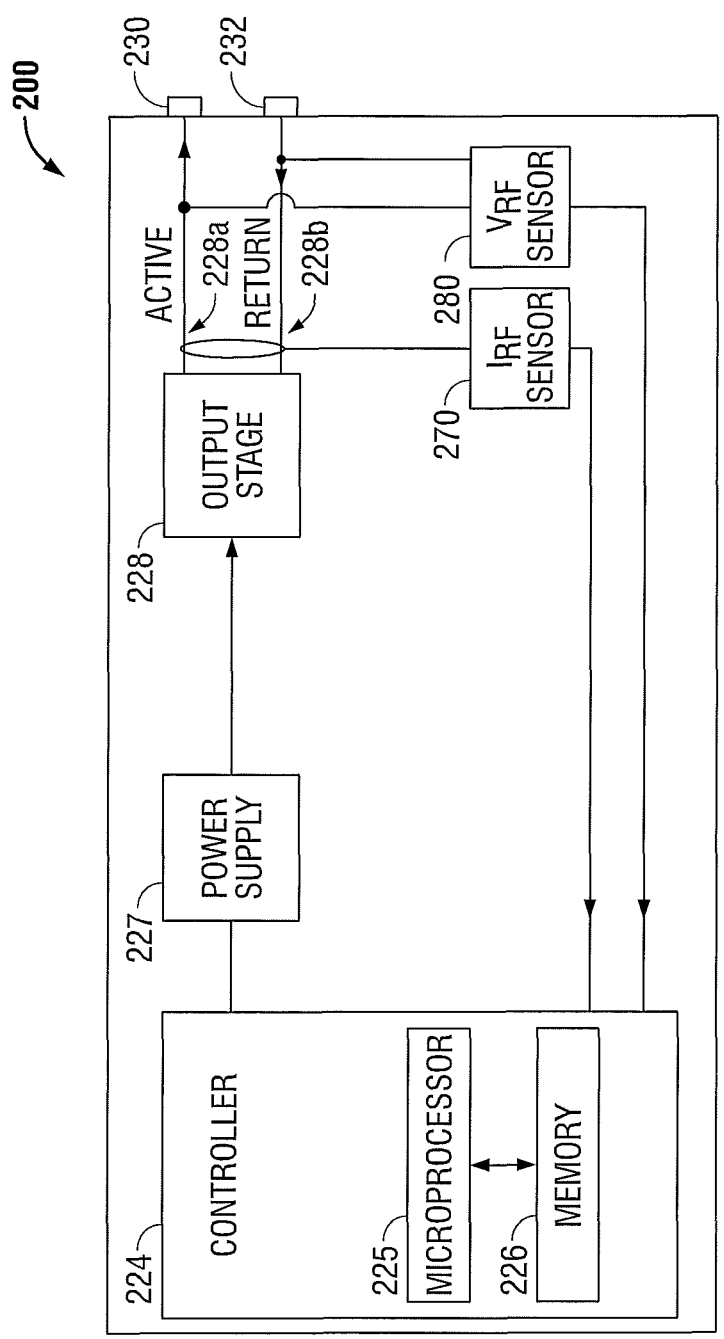
FIG. 3 is a schematic, block diagram of the electrosurgical generator of FIG. 2 according to the present disclosure.

The system 1 may also include a bipolar electrosurgical forceps 10 having one or more electrodes for treating tissue of a patient. The electrosurgical forceps 10 includes a housing 11 and opposing jaw members 13 and 15 disposed at a distal end of a shaft 12. The jaw members 13 and 15 have one or more active electrodes 14 and a return electrode 16 disposed therein, respectively. The active electrode 14 and the return electrode 16 are connected to the generator 200 through cable 18 that includes the supply and return lines 4, 8 coupled to the active and return terminals 230, 232, respectively (FIG. 3). The electrosurgical forceps 10 is coupled to the generator 200 at a connector having connections to the active and return terminals 230 and 232 (e.g., pins) via a plug disposed at the end of the cable 18, wherein the plug includes contacts from the supply and return lines 4, 8 as discussed in more detail below.

Figure 2:
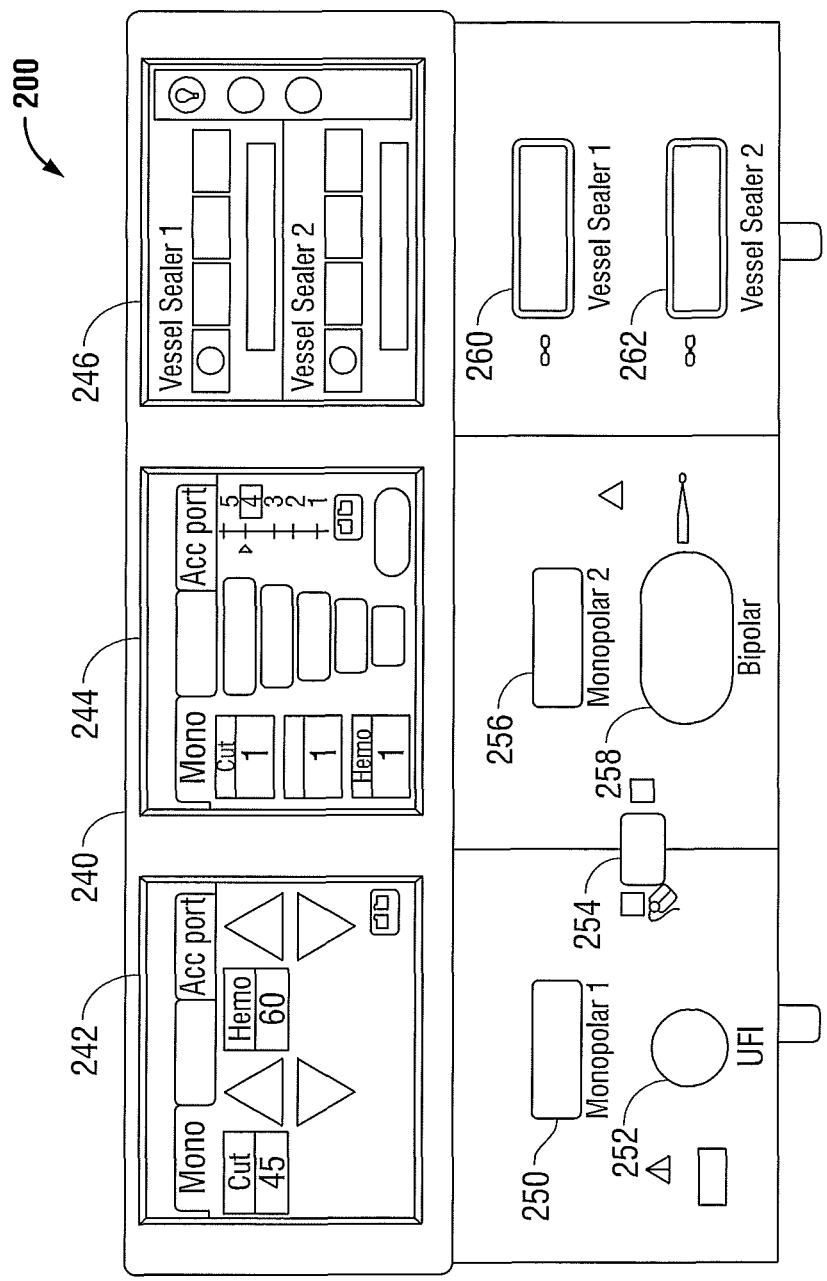
FIG. 2 is a front view of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read (e.g., scan, decode, etc.) identifying information encoded or otherwise recorded on or within the plugs or cables of the instruments. The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-transitory storage (e.g., non-volatile memory, EEPROM, etc.), which may then be coupled to or integrated into the plug. Corresponding detection devices may include, but are not limited to, bar code readers, electrical sensors, RFID readers, Hall Effect sensors, memory readers, etc. and any other suitable decoders configured to decode data.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then adjusts inputs by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. The generator 200 includes a controller 224, a power supply 227, and an output stage 228. The power supply 227 may be a direct current high voltage power supply that connects to an AC source (e.g., line voltage) and provides high voltage DC power to an output stage 228, which then converts high voltage DC power into treatment energy (e.g., ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a processor 225 operably connected to a memory 226, which may include transitory type memory (e.g., RAM) and/or non-transitory type memory (e.g., flash media, disk media, etc.). The processor 225 includes an output port that is operably connected to the power supply 227 and/or output stage 228 allowing the processor 225 to control the output of the generator 200 according to either open and/or closed control loop schemes. Those skilled in the art will appreciate that the processor 225 may be substituted by any logic processor (e.g., control circuit) adapted to perform the calculations and/or set of instructions discussed herein.

A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or output stage 228, which then adjusts the DC and/or power supply, respectively. The controller 224 also receives input signals from the input controls of the generator 200, the instrument 2 and/or forceps 10. The controller 224 utilizes the input signals to adjust power outputted by the generator 200 and/or performs other control functions thereon.

The generator 200 according to the present disclosure includes an RF current sensor 270 and an RF voltage sensor 280. The RF current sensor 270 is coupled to the active terminal 230 and provides measurements of the RF current supplied by the output stage 228. The RF voltage sensor 280 is coupled to the active and return terminals 230 and 232 provides measurements of the RF voltage supplied by the output stage 228. In embodiments, the RF current and voltage sensors 270 and 280 may be coupled to active and return leads 228a and 228b, which interconnect the active and return terminals 230 and 232 to the output stage 228, respectively. The RF current and voltage sensors 270 and 280 provide the sensed RF voltage and current signals, respectively, to the controller 224, which then may adjust output of the power supply 227 and/or the output stage 228 in response to the sensed RF voltage and current signals. Various components of the generator 200, namely, the output stage 228, the RF current and voltage sensors 270 and 280, may be disposed on a printed circuit board (PCB).

The present disclosure provides for electrosurgical generator 200 having real-time arc energy vascular coagulation control during RF-based energy delivery to the surgical site. In particular, the generator 200 is configured to control arc energy delivered to the surgical site by compensating for the monopolar arc energy variations in arc spatial length and arc impedance. This minimizes the delivered energy loss at the tissue site due to arc impedance changes and increases the intended energy delivery to the vascular bleeders and other tissue types that cause substantial variation in impedance. As used herein, the term "bleeder" refers to any tissue structure (e.g., vein, artery, etc.) that supplies blood to the treatment site.

The generator 200 according to the present disclosure also minimizes eschar and excess tissue desiccation thermal damage through arc energy control while achieving hemostasis control of perfuse vascular bleeders in vessel and organ structures such as arteries, veins, liver, and other vascular tissue structures.

Conventional electrosurgical energy sources achieve monopolar coagulation of vascular bleeders without compensating for the variations in delivered arc energy. In particular, conventional monopolar applications of RF-based energy only apply constant power control with low duty cycle, high voltage RF waveforms without compensating for variations in the changing spatial arc length and arc impedance. These variations are due changes in the distance between the tissue and the electrode due to surgeon manipulation of the surgical instrument to the bleeder site. As a result, treatment energy for sealing vascular bleeders is adversely impacted, thereby affecting the quality of tissue desiccation and coagulation.

In conventional generators, the use of constant power control sets the high voltage to initiate an arc, but as the arc distance changes so does the arc impedance, as described above. Spatial arc length variations increase the arc impedance and lower the current delivered to the bleeder under power control. The lower delivered current, in turn, reduces the power and energy delivered to the tissue which is needed for bleeder coagulation. The increased spatial arc length may result in extinguishing the arc and energy loss to the tissue bleeder site. Conversely, changes in the spatial arc length as the user maneuvers the instrument closer to the tissue bleeder decreases the arc impedance thereby increasing the RF current delivered under constant power control. The increase in delivered RF current results in an increase of delivered tissue power for bleeder coagulation, resulting in potential excess eschar and tissue desiccation thermal damage. Thus, it is desirable to control energy delivery to vascular bleeders to maximize energy delivery resulting in efficient coagulation while minimizing eschar build-up.

The present disclosure provides for a system and method for controlling applied RF-based arc energy using a combination of power, current and voltage control to compensate for the variations in arc impedance and the distance between the electrode and the vascular bleeder. Initially, the RF power is set to a desired level having sufficient voltage to initiate an arc. The generator 200 is further configured to dynamically and in real-time switch from power to current control to sustain the arc during a monopolar activation command, independent of the variations in arc impedance or spatial arc length. The generator 200 is also configured to switch to the preset power and voltage control values and deliver an improved control of delivered energy to vascular bleeders for improved desiccation and diminished eschar build up while achieving hemostasis in vessel and organ structures during surgical procedures.

The present disclosure also provides for a system and method for controlling monopolar arc energy vascular coagulation using a real-time algorithm. The algorithm may be implemented as computer-readable source code stored in the memory 226 and executable by the processor control of the applied RF based arc energy using a combination of power, current and voltage control to compensate for the variations in arc impedance and the surgeon spatial instrument proximal distance to the vascular bleeder.

The user commences operation of the generator 200 by setting desired electrosurgical settings, such as power, voltage, current, duty cycle and the like. The settings may be combined into a uniform intensity setting that adjusts one or more of those values accordingly. Once the procedure is commenced, the generator 200 outputs energy using power control to generate the arc. In particular, the controller 224 signals the output stage 228 to output an electrosurgical waveform in response to the power control mode during which the controller 224 signals the output stage 228 to deliver electrosurgical energy at a predetermined power level to generate an arc between an active electrode and tissue. During operation, the sensors 270 and 280 continuously measure tissue and/or energy properties and provide the measurements to the controller 224. Measured properties, include, but are not limited to, impedance, voltage, current, power, time duration, as well as instantaneous, average, root-mean-square values, and combinations thereof. Based on those measurements the controller 224 determines whether to switch to a current control mode, during which controller 224 signals the output stage 228 to deliver electrosurgical energy at a predetermined or dynamically adjusted current to sustain the arc.

Figure 4:
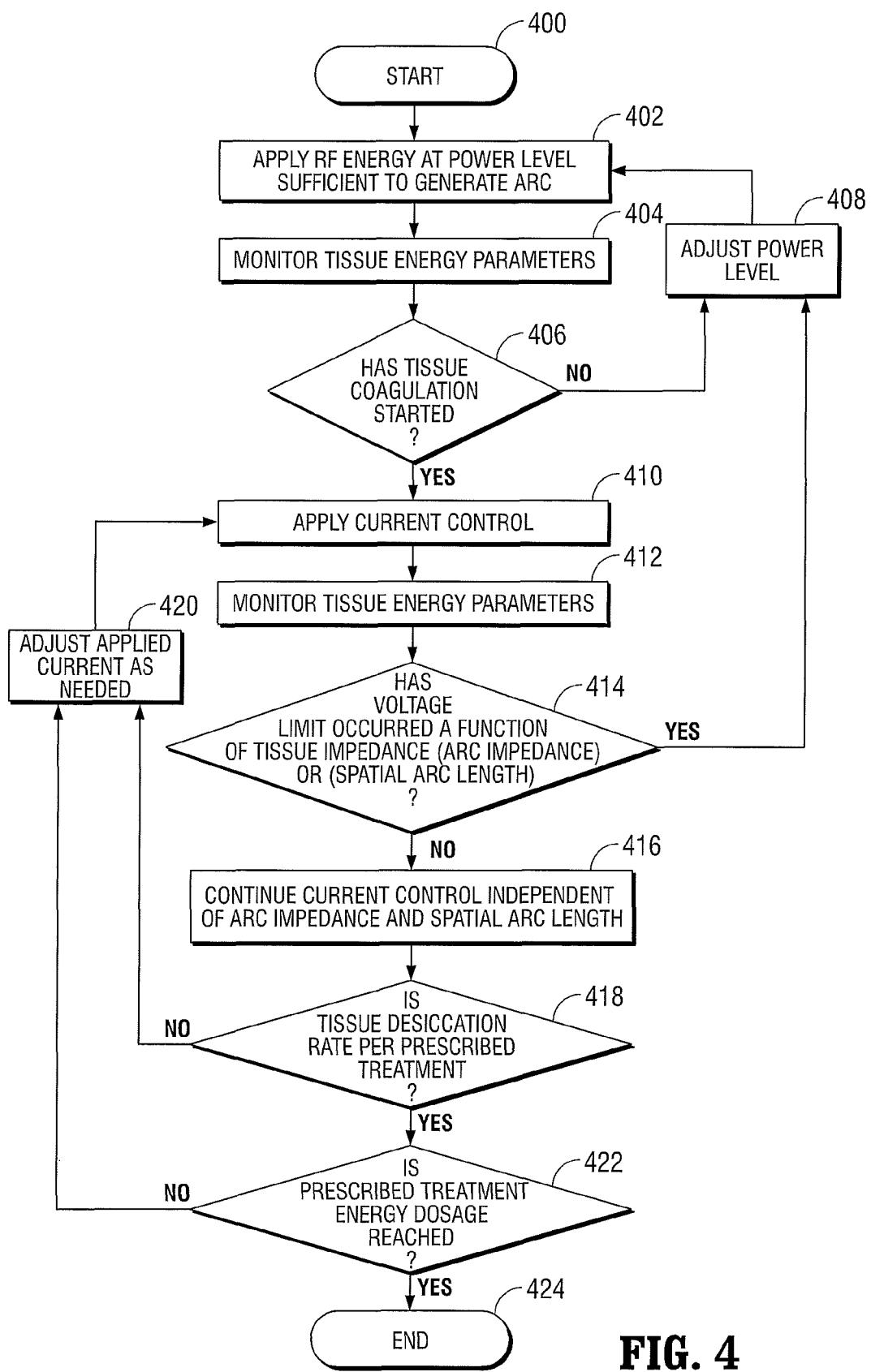
FIG. 4 is a flow chart of a method according to the present disclosure.

FIG. 4 illustrates a method for controlling the delivery of RF energy according to the present disclosure. In step 400, the generator 200 starts a process whereby the monopolar electrosurgical instrument 2 is brought in proximity to tissue to deliver controlled arc energy to achieve vascular coagulation during RF based treatment of perfuse vascular bleeders.

In step 402, the generator 200 initiates power delivery using power control at predetermined power level sufficient to generate an arc. As used herein, "power control" denotes controlling output energy of the generator 200 to achieve a desired output power including, but not limited to, constant power, non-linear power curve, and combinations thereof. During power control mode, tissue energy parameters such as power, voltage, current, tissue impedance and application time are monitored in step 404. In step 406, a decision is assessed based on the monitored tissue energy parameters of step 404, to determine whether tissue coagulation has started. In embodiments, the decision may be based on at least one or more parameter evaluations including, but not limited to, a change in the tissue impedance, a change in the level of tissue RF conduction current, a change in the level of applied RF voltage, a change in the energy level applied to the tissue, and combinations thereof. If the decision result, as computed and assessed by the microprocessor 225 residing in the host controller 224, identifies that tissue coagulation has started, then generator 200 switches in real-time from power control mode to current control mode in step 410. As used herein, "current control" denotes controlling output energy of the generator 200 to achieve a desired output current including, but not limited to, constant current, non-linear current curve, and combinations thereof. If it is determined that the coagulation has not started as determined by step 406, then in step 408 the controller 224 signals a request to adjust the power level in step 402, such that the energy level is adjusted accordingly to initiate tissue coagulation and generate an arc.

In step 410, current mode control provides continuous tissue coagulation independent of changes in the arc impedance or the spatial arc length due to distance changes of the instrument relative to the tissue site. In this manner, coagulation control of vascular bleeders can receive an appropriate level of energy to achieve hemostasis. Step 412 monitors the tissue energy parameters described above in step 404 to determine the precise level of energy coagulation control. This is accomplished by adjusting the applied energy parameters, previously identified in a static or dynamic manner to achieve the tissue specific level of hemostasis control.

While the tissue energy parameters are monitored in step 412, step 414 continuously monitors the rate of change in vascular tissue coagulation to determine if the sensed tissue voltage is rapidly approaching the system voltage limit dependent on tissue type. During current control, the impedance of vascular vessel structures increases at a rapid rate such that the applied voltage also rises rapidly at the tissue site. In addition step 414 is also monitoring the rate of change of the arc impedance as well as the spatial arc length, as they also may change during energy activation due to surgeon proximal shifts in instrument position, such that the monitored voltage may increase. Controller 224 monitors these voltage changes to differentiate the change due to tissue vascular coagulation with the changes due to spatial distance variations.

Microprocessor 225 may include an appropriate discrimination filter under algorithm control to differentiate voltage changes due to tissue coagulation or instrument positional change. Tissue coagulation with applied arc energy changes rapidly as compared to the slower changes of the arc impedance due instrument positional variations. This difference allows for determination whether the voltage changes are caused by the spatial variation or tissue impedance. In this manner the tissue coagulation treatment energy can be better controlled to achieve the desired hemostasis as correlated to specific tissue types.

If the system voltage limit is reached, the controller 224 switches back to power control, namely, to step 408, to adjust the power level thereby providing appropriate energy dosage for tissue coagulation. In step 414, if the voltage limit is not reached, current control continues as indicated in step 416. Under current mode control, the rate of tissue vascular desiccation is monitored in step 418 to minimize the degree of vascular charring and eschar buildup. If the decision in step 418, as determined by the controller 224, identifies that the rate of vascular desiccation is insufficient, then the controller 224 proceeds to step 410 via step 420 to adjust the rate of current control such that proper tissue hemostasis is achieved.

Conversely, if tissue desiccation is proceeding according to the prescribed treatment energy protocol then controller 224 proceeds to block 422 to determine if the appropriate level of energy control has been reached. If no, then the controller 224 proceeds to block 420 to initiate a request to adjust the applied current as needed by signaling step 410. If in step 422, the controller 224 determines that the appropriate level of vascular treatment energy has been reached by calculating total amount of energy deposited into tissue to achieve tissue hemostasis, then the algorithm control is complete as indicated by step 424 and the energy delivered to the vascular bleeder is terminated.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for delivering electrosurgical energy, comprising:
   an electrosurgical instrument comprising at least one electrode; and
   an electrosurgical generator coupled to the electrosurgical instrument, the electrosurgical generator comprising:
   an output stage configured to generate electrosurgical energy; and
   a controller coupled to the output stage, the controller configured to control the output stage to output electrosurgical energy at a predetermined power control mode having a first current level to generate an arc between the at least one electrode and tissue and to output electrosurgical energy at a predetermined current level control mode having a second current level different from the first current level once the arc is generated to sustain the arc.

2. The system according to claim 1, wherein the electrosurgical generator further comprises:
   a sensor configured to measure at least one of a tissue or an energy property.

3. The system according to claim 2, wherein the at least one of the tissue or the energy property is selected from the group consisting of impedance, root-mean-square voltage, average voltage, instantaneous voltage, current, power, root-mean-square current, average current, instantaneous current, root-mean-square power, average power, instantaneous power, and combinations thereof.

4. The system according to claim 2, wherein the controller is coupled to the sensor, the controller configured to switch between a power control mode and a current control mode in response to the at least one of the tissue or the energy property, wherein during the power control mode the output stage is delivering electrosurgical energy at the predetermined power level to generate the arc between the at least one electrode and tissue and during the current control mode the output stage is delivering electrosurgical energy at the predetermined current level once the arc is generated to sustain the arc.

5. The system according to claim 4, wherein the sensor is further configured to measure voltage applied to the tissue and the controller is configured to determine whether the voltage is below a predetermined voltage threshold.

6. The system according to claim 5, wherein the controller is configured to maintain the current control mode in response to the voltage being below the predetermined voltage threshold.

7. A system for delivering electrosurgical energy, comprising:
   an electrosurgical instrument comprising at least one electrode; and
   an electrosurgical generator coupled to the electrosurgical instrument, the electrosurgical generator comprising:
   an output stage configured to generate electrosurgical energy;
   a sensor configured to measure at least one of a tissue or an energy property; and
   a controller coupled to the output stage and the sensor, the controller configured to switch between a power control mode and a current control mode in response to the at least one of the tissue or the energy property, wherein during the power control mode the output stage is delivering electrosurgical energy at a predetermined power level having a first current amplitude to generate an arc between the at least one electrode and tissue and during the current control mode the output stage is delivering electrosurgical energy at a predetermined current level having a second current amplitude different from the first current amplitude once the arc is generated to sustain the arc.

8. The system according to claim 7, wherein the sensor is further configured to measure voltage applied to the tissue and the controller is configured to determine whether the voltage is below a predetermined voltage threshold.

9. The system according to claim 8, wherein the controller is configured to maintain the current control mode in response to the voltage being below the predetermined voltage threshold.

10. The system according to claim 7, wherein the at least one of the tissue or the energy property is selected from the group consisting of impedance, root-mean-square voltage, average voltage, instantaneous voltage, current, power, root-mean-square current, average current, instantaneous current, root-mean-square power, average power, instantaneous power, and combinations thereof.

11. A method for delivering electrosurgical energy, comprising:
    delivering electrosurgical energy at a predetermined power control mode having a first current level to generate an arc between at least one electrode and tissue during a power control mode; and
    delivering electrosurgical energy at a predetermined current control mode having a second current level different from the first current level once the arc is generated to sustain the arc during a current control mode.

12. The method according to claim 11, further comprising:
    measuring at least one of a tissue or an energy property.

13. The method according to claim 12, further comprising:
    switching between the power control mode and the current control mode in response to the at least one of the tissue or the energy property.

14. The method according to claim 12, wherein the at least one of the tissue or the energy property is selected from the group consisting of impedance, root-mean-square voltage, average voltage, instantaneous voltage, current, power, root-mean-square current, average current, instantaneous current, root-mean-square power, average power, instantaneous power, and combinations thereof.

15. The method according to claim 13, further comprising:
    measuring a voltage applied to the tissue and determining whether the voltage is below a predetermined voltage threshold.

16. The method according to claim 15, further comprising:
    maintaining the current control mode in response to the voltage being below the predetermined voltage threshold.

* * * * *